United States Patent [19]

Christian

[11] Patent Number: 4,502,481
[45] Date of Patent: Mar. 5, 1985

[54] DEVICE FOR MANUALLY VENTILATING A PATIENT

[76] Inventor: Pamela H. Christian, 1726 Loree Dr., Dallas, Tex. 75228

[21] Appl. No.: 466,375

[22] Filed: Feb. 15, 1983

[51] Int. Cl.³ .......................................... A61M 16/00
[52] U.S. Cl. .............................................. 128/205.24
[58] Field of Search ...................... 128/203.14, 203.28, 128/203.29, 204.18, 204.21, 204.24, 204.25, 205.12, 205.13, 205.14, 205.15, 205.16, 205.17, 205.18, 205.24, 205.25, 207.14, 207.15

[56] References Cited

U.S. PATENT DOCUMENTS

| 2,918,917 | 12/1959 | Emerson | 128/205.24 |
| 3,307,542 | 3/1967 | Andreasen | 128/205.15 |
| 3,814,091 | 6/1974 | Henkin | 128/205.17 |
| 3,949,749 | 4/1976 | Stewart | 128/204.24 |
| 3,957,047 | 5/1976 | Freytag et al. | 128/204.24 |

Primary Examiner—Henry J. Recla
Attorney, Agent, or Firm—T. D. Copeland

[57] ABSTRACT

A ventilation device for manually ventilating a patient having an inspiratory tube connected between a source of breathing gas and a patient adaptor and an expiratory tube connected between the patient adaptor and a two-way exhaust valve. The exhaust valve includes two flow paths each having a normally closed overpressure valve therein and an outlet communicating to atmosphere. The valves are adjusted respectively for positive peak inhalation pressure and positive end expiration pressure. The outlet adjacent the valve biased for positive end expiratory pressure is occludible to initiate the insufflation phase and regulate the peak inspiratory pressure.

11 Claims, 6 Drawing Figures

DEVICE FOR MANUALLY VENTILATING A PATIENT

BACKGROUND OF THE INVENTION

Prior ventilation devices for patients with breathing difficulties include the following known patents and publications:

U.S. Pat. No. 3,842,828; Pediatric Ventilator; F. M. Bird;
U.S. Pat. No. 3,915,164; Pediatric Ventilator; F. M. Bird;
U.S. Pat. No. 3,967,619; Apparatus & Method for Intermittent Mandatory Ventilation; E. W. Story, et al;
U.S. Pat. No. 3,993,059; Device for Ventilating a Patient; U. H. Sjostrand;
U.S. Pat. No. 4,197,843; Volume Limiting Ventilator; F. M. Bird;
Puritan Bennett brochure, Form No. 433805, dated 12-1-70, entitled "Modified Mask Elbow for Infant Resuscitation and Anesthesia".
Puritan Bennett Operating & Maintenance Instructions, Form No. 433804, dated 10-30-78, entitled "Non-Rebreathing Pressure Relieving Elbow".

each of which discloses inventions useful in this field. However, none of the devices disclosed will perform the needed function of a light weight, easily portable unit that provides a continuous positive pressure insufflation device, the patient attaching end of which may be inserted into an incubator, isolette, radiant warmer bed, or similar infant receptacle, so that the operator is removed from the infant's vicinity, but yet has complete control of its breathing rate and insufflation and exsufflation pressures. This control is additionally totally manually applied in a non-exertion method, so that no mechanical, pneumatic or electrical machinery is necessary, and the entire unit is easily carried by one nurse on an ambulance and into a hospital to accommodate an infant whose breathing needs assisting.

GLOSSARY

In the field of ventilation of patients, there are many terms of art and acronyms that are used, or may be used, to simplify the designation of conditions encountered or desired. These include the following:

Breathing Gas—A mixture of air and oxygen in controlled percentages.
CMV—Continuous mechanical ventillation.
CPAP—Continuous positive airway pressure (positive pressure in the airway during the inhalation cycle).
CPPB—Continuous positive pressure breathing.
Endotracheal Tube—a small diameter open tube that delivers breathing gas thru a patient's mouth or nose.
Expiratory Pressure—The breathing gas pressure in the ventillation system during the exhalation cycle.
Exsuffolation—Ending of the breathing cycle.
FiO$_2$—Fraction of inspired oxygen is the percentile of oxygen in the breathing gas mixture.
IMV—Intermittent mandatory ventilation.
Inspiratory Pressure—The breathing gas pressure in the ventillation system during the inhalation cycle.
Insuffolation—Beginning of the breathing cycle.
Isolette—An infant receptacle similar to an incubator.
Lumen—An opening, such as the interior of a breathing tube.
Nebulizer Device—Device to increase the moisture content in the breathing gas.
Neonates—Infants of recent birth, many of whom may be subject to lung collapse without a continuous pressure breathing gas.
Occlude—To close off an opening or port.
Over-pressure Valve—Any valve that provides a controllable restriction to the flow of fluid passing therethru, whereby back pressure is increased.
PEEP—Positive end expiratory pressure in the airway at the end of the patient's expiration cycle.
Positive Pressure Ventilation—A condition where there is always some pressure above atmospheric in the airway when the ventilation system is in use.
Tracheostomy Tube—A small diameter open tube that delivers breathing gas thru a surgically cut opening in the trachea (wind pipe).
Ventillation—Assisted breathing with mechanical implementation.

SUMMARY OF THE INVENTION

The present invention refers to a device to be connected to a patient by means of an endotracheal tube, tracheostomy tube, or a breathing mask. The device being powered by a source gas (a selected mixture of air and oxygen) in a constant flow, pressure limited, and manually time cycled ventilator. The device according to the invention is especially intended for ventilating neonates (infants of recent birth).

When ventilating a patient by means of a manual lung ventilator it is desired to have variable, yet precisely measured parameters. It is exceedingly desirable that during the ventilation by means of the manual ventilator, the patient has also the possibility to breathe spontaneously and that the spontaneous breathing is not prevented by or in conflict with the ventilation by means of the manual ventilator used. With the capability described above, the manual ventilator can provide IMV (Intermittent Mandatory Ventilation).

When ventilating a patient with positive pressure ventilation, it is extremely important to know the level of inspiratory pressure delivered to the patient. The present invention can be adjusted to maintain the positive pressure being applied to the patient by means of an adjustable over-pressure valve. This pressure (Peak Inspiratory Pressure) is maintained at a level which the operator sets, and continuously monitors by means of a pressure manometer which is in line at the proximal airway.

Further, it is desirable to be able to deliver and maintain an adjustable end expiratory pressure by means of an adjustable over-pressure valve at the end of the expiratory phase of the ventilation. This end expiratory pressure is a predetermined over-pressure adjusted by another adjustable over-pressure valve in line with the manual ventilator. This end expiratory pressure may be used during positive pressure ventilation, i.e., PEEP (Positive End Expiratory Pressure), or may be used without positive pressure ventilation, i.e., CPAP (Continuous Positive Airway Pressure). When CPAP is used, this means that the infant is continuously supplied with the desired breathing gas under a predetermined over-pressure, but that the patient himself has to do the breathing work by means of spontaneous breathing. This predetermined over-pressure (PEEP or CPAP) is monitored by the pressure monitor in line with the manual ventilator.

The present invention is a manually time cycled ventilator. The operator is in control of the rate at which the positive pressure ventilation is to be delivered. The rate is timed by the operator as well as the duration of the gas being delivered to the patient during the inspiratory phase of ventilation, i.e., inspiratory time. The operator accomplishes this by intermittently occluding an adjustable over-pressure valve for the duration of time necessary to achieve the desired inspiratory time and rate. With this over-pressure valve occluded, all gas flow is directed to the patient and therefore limited only by the other over-pressure valve which is preset to relieve the pressure (Peak Inspiratory Pressure) at the desired level.

It is of extreme importance to deliver precise oxygen concentrations in the breathing gas powering the manual ventilator. Further, it would be of great advantage to control and monitor the $FiO_2$ (Fraction of Inspired Oxygen) being delivered to the patient. The $FiO_2$ may be blended together with air and oxygen which is combined thru tubing as shown in FIG. 2 or may be premixed in a commercial blender. To determine the precise $FiO_2$, an oxygen analyzer is placed in series with the manual ventilator "V" shown in FIG. 2.

When ventilating an infant with the manual ventilator, it is desirable to add humidification to the breathing gas. This is provided thru the humidifier shown in FIG. 2.

In summary, the device described here may be used simply to deliver CPAP—continuous positive airway pressure by way of a patient connector such as an endotracheal tube, a trachcostomy tube, or a breathing mask, where the patient still has the ability to breathe spontaneously at the rate and depth in which he desires, with precise $FiO_2$ concentrations, and with the humidity which may be added.

One can easily and quickly switch from the CPAP mode of therapy in which the patient breathes spontaneously to aiding the patient with CPPV—continuous positive pressure ventilation. In this mode of therapy, the patient receives positive pressure ventilation at the level of inspiratory pressure adjusted on the over-pressure valve. The rate (breaths per minute) and inspiratory time (duration of occlusion) is accomplished manually by the operator, by simply placing and holding his finger over the exit port of the in-line valve, without any further manipulation of the device. The patient may continue to breathe spontaneously thru the circuit during positive pressure ventilation due to the continuous flow of breathing gas thru the device, i.e., IMV—intermittent mandatory ventilation. In this mode of therapy, CPPV, the patient may also continue to receive end expiratory pressure—PEEP.

In many small hospitals in this country the only means of ventilating newborns and infants is the use of a manual resuscitation bag. The use of such bag becomes inadequate when providing long term ventilation support to critical infants.

When comparing the device described here to a resuscitation bag, the following advantages are noted: continuous positive airway pressure (CPAP) and/or positive end expiratory pressure (PEEP) may be provided; precise peak inspiratory pressures (usually in the range 10-60 cm/water are delivered; precise oxygen concentrations ranging from 21 -100% are easily provided; the device provides intermittent mandatory ventilation—IMV as the patient may breathe spontaneously; humidification as is desired may be provided; virtually no fatigue is encountered by the operator; and the infant may be ventilated without the operator being extremely close to the patient since controls for adjustment and ventilation may be outside the isolette or radiant warmer bed or incubator.

It was to solve the problem of providing adequate ventilation to newborns and infants in hospitals without mechanical neonatal ventilators that the concept of the manual ventilation device described here was developed. With such a device these hospitals can provide optimal ventilatory support while awaiting the arrival of the tertiary (signifying the highest of the three levels of infant care) center's transport team with their more sophisticated equipment. In addition, the tertiary center will find this device useful during transport of patients since this device is extremely portable. This advantageous use is highlighted when more than one patient requires transportation, or when the vehicle's mechanical ventilator fails to function.

BRIEF DESCRIPTION OF THE DRAWINGS

In the following, the invention will be described in detail in connection with the attached drawing which illustrates some embodiments of the invention, whereby.

DESCRIPTION OF THE PREFERRED EMBODIMENTS

Figure 1:
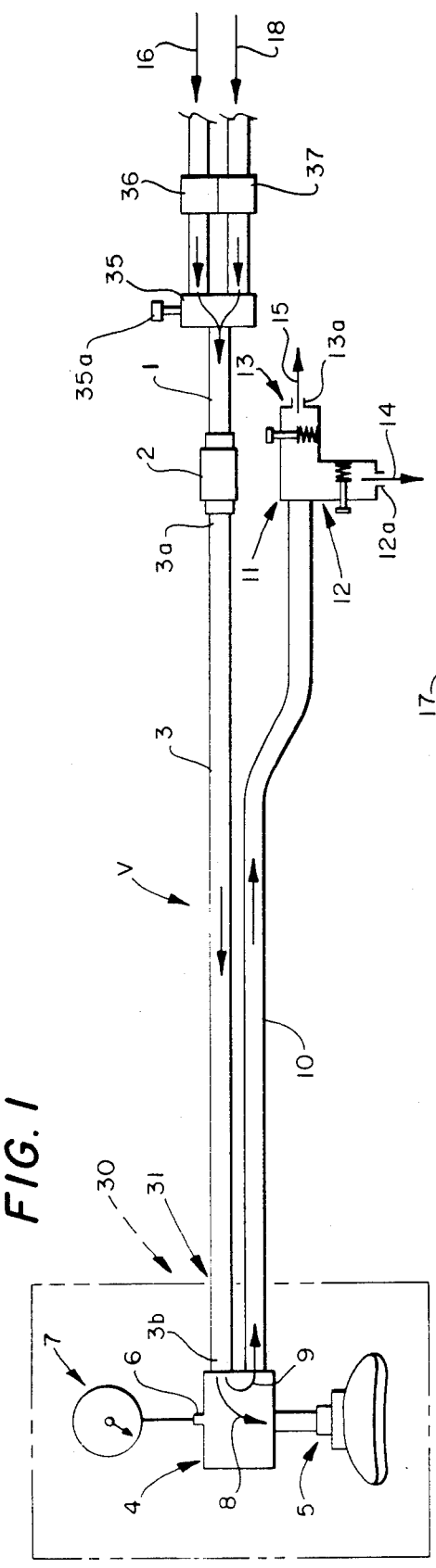
FIG. 1 schematically shows a first embodiment of arrangement according to the invention, which allows ventilation of a patient thru a continuous flow double lumen (opening) circuit.

The device according to this invention is a constant flow, pressure limited, manually time cycled, neonatal ventilator. The device may be powered by breathing gas flow as low as 10 liters per minute (l/m) without accumulating carbon dioxide in the patient circuit.

The source gas powering the device enters the inspiratory side of the double lumen (opening) circuit at a given flow rate set by the operator. With the flow rate fixed, pressure in the circuit is determined by the resistance in the circuit, diameter of the tubing used and the size of any orifices. This circuit has two variable orifices in the form of over-pressure valves to control the peak inspiratory pressure and the level of end expiratory pressure.

The breathing gas from source 1 enters the inspiratory tube 3 through the connection piece 2 at the end 3*a* of tube 3. The breathing gas from source 1 follows the inspiratory tube 3 to connect with a standard 15 mm diameter adaptor 4 at the end 3*b* of tube 3. The patient adaptor 4 is connected to a conventional endotracheal tube, a tracheostomy tube, or a breathing mask, all referred to generally as a patient connector 5, which is there applied to the patient. The patient adaptor 4 is provided with a fitting 6 for the connection to a manometer 7 for measuring and registering the pressure at the upper end of the patient connector 5. The ends of tubes 3 & 10, as well as adaptor 4 and connector 5, and the infant being treated may all be within an incubator or isolette 30. The tubes are entered through a small access opening 31 in the side of the infant container.

During the insufflation phase of the manually cycled ventilator here described, the breathing gas from source 1 enters through the inspiratory tube 3 into the patient connector 5, and into the lungs of the patient as indicated by the arrow 8. During the following exsufflation phase of the manually cycled ventilator, the consumed breathing gas will, due to the elasticity of the lungs of the patient, be pressed out of the lungs through the patient connector 5, and further through the expiratory tube 10 of the double lumen circuit. The breathing gas will flow from the expiratory tube 10 through the two valve end fitting 11 out into the surrounding atmosphere through the over-pressure valves 12 and 13.

Due to the ventilator described here as being a constant flow device, the breathing gas will enter the lungs of the patient, as indicated by arrow 8, when the over-pressure valve 13 is occluded to initiate the insufflation phase. Pressure in the circuit will rise to the level adjusted to release the over-pressure valve 12, which was previously set by the operator. The flow of breathing gas from source 1 will continue to flow past the patient adaptor 4 into the expiratory tube 10, as indicated by arrow 9, and out the over-pressure 12 to the surrounding atmosphere, indicated by arrow 14.

Furthermore, if the patient so wishes, he can breathe spontaneously, previously described as IMV capability. The patient can breathe spontaneously at the rate and depth he wishes due to the continuous flow thru the circuit indicated by arrow 9.

The expiratory tube 10 is provided with two over-pressure valves 12 and 13, both having adjustable orifices. Over-pressure valve 13 is opened to provide the level of end expiratory pressure desired with the flow rate fixed. This is accomplished by attaching the patient adaptor 4 to a test lung (not shown), which simulates lung compliance, and then closing the over-pressure valve 12. The level of end expiratory pressure (CPAP and/or PEEP) is adjusted by opening the over-pressure valve 13, and observing the pressure reading on the manometer 7 in line at the patient adaptor 4. This over-pressure valve 13 has a multiple function: On the one hand it generates the level of end expiratory pressure is held constant, given a fixed flow rate. On the other hand, it makes possible the exhalation of the patient, as indicated by arrow 15.

The over-pressure valve 12 is adjusted to obtain the level of peak inspiratory pressure desired to ventilate the patient. This is accomplished by attaching the patient adaptor 4 to a test lung, as previously done, and manually occluding the over-pressure valve 13. When occluding the over-pressure valve 13, breathing gas must exit through the over-pressure valve 12, indicated by arrow 14, since it is the only outlet to the atmosphere from this circuit. At this time, the over-pressure valve 12 may be adjusted to release pressure at the desired level by observing the manometer 7 in line at the patient adaptor 4.

Now with the breathing gas entering the inspiratory tube 3 at a fixed flow rate, the peak inspiratory pressure has been adjusted with the over-pressure valve 12, and the level of end expiratory pressure has been adjusted with the over-pressure valve 13, the patient may now be manually ventilated. Manual ventilation of the patient is accomplished by intermittently occluding the over-pressure valve 13 at the desired rate (the number of occlusions per minute) and inspiratory time (duration of occlusion), which is accomplished the operator's finger closing and opening the port opening 13a of valve 13. When the over-pressure valve 13 is occluded, the pressure in the circuit rises until it reaches the level adjusted on the over-pressure valve 12, thereby opening this valve and exiting the breathing gas to the atmosphere through the valve 12, indicated by arrow 14. This is the inspiratory phase of ventilation. When the operator manually releases the over-pressure valve 13, the expiratory phase takes place as breathing gas exits through the over-pressure valve 13, which is the path of least resistance, and indicated by arrow 15.

Figure 2:
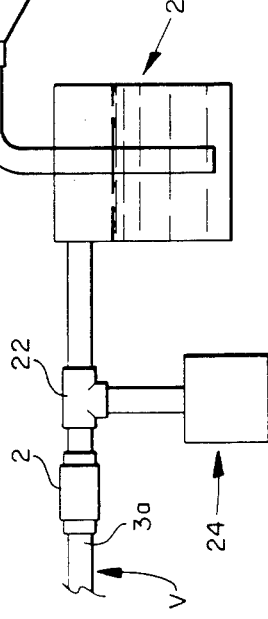
FIG. 2 schematically shows a breathing gas source of another embodiment of this invention.

In FIG. 2, the mixing of the source gases used to comprise the breathing gas is shown. An air source 16, and an oxygen source 18 should be mixed together to acheive the desired FiO$_2$ (fraction of inspired oxygen). The gas sources may either be from compressed gas tanks or from wall connections piped into the hospital from a large volume reservoir within the hospital system. An air flow meter 17 and oxygen flow meter 19 are attached to the gas sources in order to measure the gas flow used. Small bore tubing 23 from each gas source can be blended together with a "Y" fitting 20. From here the blended gases may enter a humidification or nebulizer device 21, or may simply be attached to the connection piece 2 to there enter the inspiratory tube 3a of the described ventillation device V.

As previously disclosed, it is of extreme importance to deliver precise oxygen concentrations in the breathing gas powering the manual ventilator. The only accurate means of determining the oxygen concentration being delivered to the patient is the use of an oxygen analyzer 24. This oxygen analyzer may be placed into the operating circuit through an adapter fitting 22.

Figure 3A:
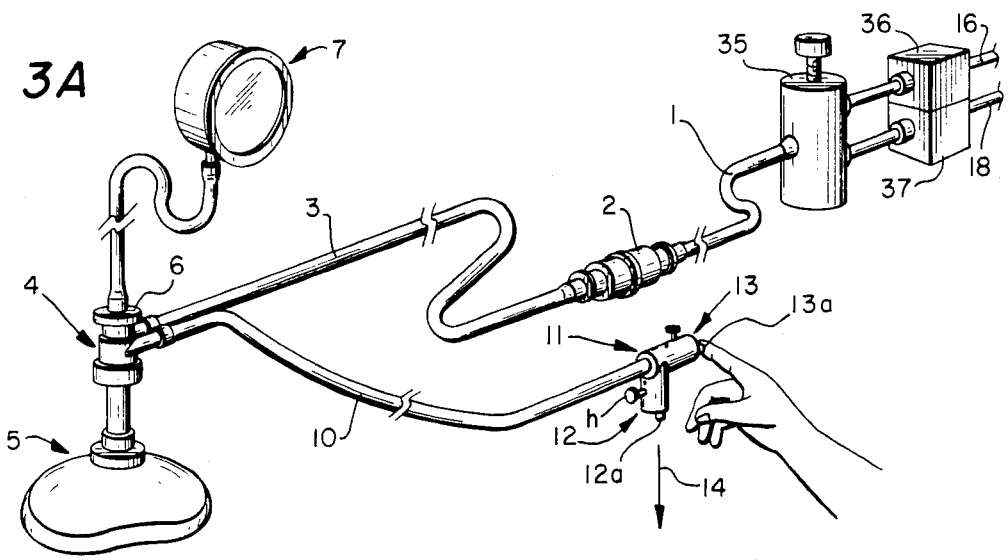
FIG. 3A shows the hardware assembly of another embodiment of the ventilation device of this invention.
Figure 3B:
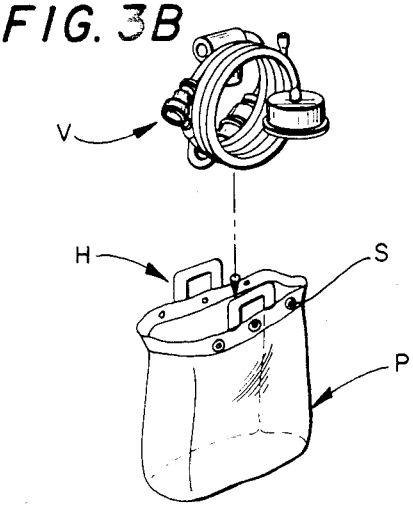
FIG. 3B shows the device of FIG. 3A in its stowed condition.

FIG. 3A shows an embodiment of this invention that is comprised exclusively of light weight plastic flexible tubing, and light weight fittings and other light weight parts up to and including connector piece 2. The balance of the system, i.e., parts 1, 16–24 & 35–37, etc., or equivalents, are available at most hospitals and on most ambulances, so that with this portable system V, which we identify as all of the parts from connector 2 to end fitting 11, inclusive, can be conveniently rolled up into a compact assembly and slipped into a light weight, usually clear plastic, easy to carry package P, which is closed with snap fasteners S and carried by handles H, all as seen in FIG. 3B.

Figure 4:
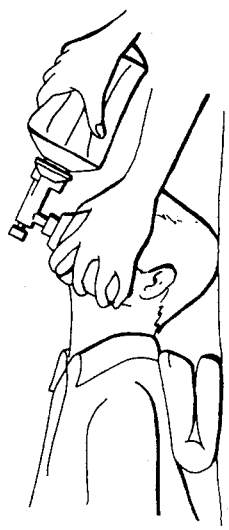
FIG. 4 is a prior art device for manual ventilation.

FIG. 4 shows one of the common methods and apparatus used in the prior art to ventillate a person in need of breathing assistance. In this instance the operator must continuously squeeze the ventilator bag using moderate strength for sometimes long periods of time. The beneficial comparison between the very slight movement of a single finger using the instant invention, and the full hand squeeze of the prior art, will be instantly recognizable. Particularly is this true in remote locations, where relief assistance simply may not be available.

Figure 5:
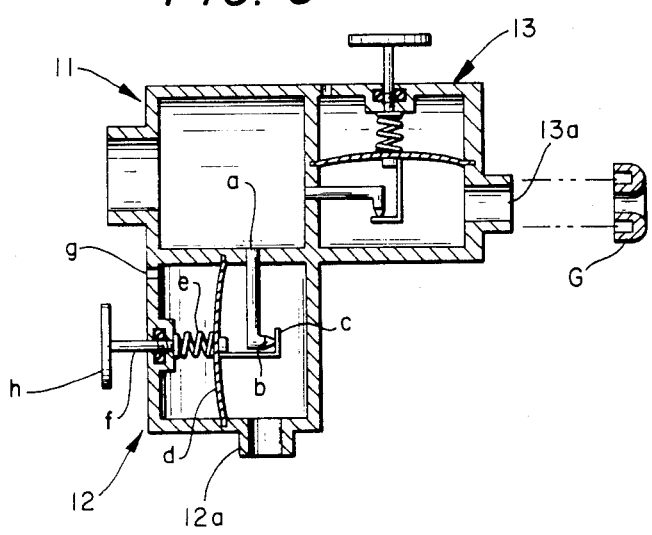
FIG. 5 is an enlarged cross sectional detail view of the two valve end fitting used in the manual control of this system.

FIG. 5 shows the details of the type of end fitting 11 that includes over-pressure valves that I propose for this installation. The housing itself is "L" shaped with an entrance chamber which directly connects to each over-pressure valve 12 & 13 so that air under pressure will take to inlet tube a to the valve requiring the lowest relief pressure to cause it to exit through ports 12a or 13a. Normally the pressurized gas would flow from the entrance chamber through valve 13 and out port 13a whenever the gas pressure exceeded the normally closed resistance of valve 13. However, when the operator's finger closes port 13a, no flow is permitted through valve 13 and the pressure backs up and increases in tubing 10, and it increases the pressurized flow through patient connector 5, until the pressure build up in the system exceeds the pressure required to open valve 12 by moving the lip of arm C that normally closes nozzle b of inlet tube a. This pressure is determined by rotating threaded valve stem handle h in the direction to place or relieve tension on leaf spring d which is indirectly connected to threaded stem f through coil spring e. Small port g permits atmospheric pressure to exist in the portion of the chamber including spring e to permit more accurate calibration of the pressure cutoff points. When the operator's finger is removed from port 13a, the gas flow will pass through the lower pressure valve 13, and valve 12 will close off again, until its threshold pressure is again reached or exceeded.

In another embodiment, end fitting 11 could comprise two separate conventional gate or other type valves, wherein the back pressure would be determined by the amount of area exposed within the valve through adjustment of the valve stem, and wherein the opening of the in line valve could be precisely axial with the expiratory tube.

A grommet type end fitting G may be placed over the open end of port 13a to increase operator comfort when occluding the open port by finger movement.

What is claimed is:

1. A device for the manual ventillation of a patient, comprising:
   a. an inspiratory tube having a bore completely therethrough,
   b. said inspiratory tube having means at one end thereof adapted to be connected to a breathing gas source,
   c. adaptor means defining first and second flowpaths,
   d. said inspiratory tube having its opposite end attached to said adaptor means and communicating with said flow path,
   e. a patient connector attached to said adaptor means for receiving breathing gas from one of said paths for inhalation by the patient, and for returning patient exhalation of said breathing gas to said second flowpath,
   f. an expiratory tube, having a bore completely therethrough connected at one of its ends to said adaptor means and communicating with said second flowpath to receive said breathing gas when exhaled by the patient,
   g. a valve housing having two sections each having an inlet connected to the other end of said expiratory tube and an outlet, and comprising an adjustable, normally closed over-pressure valve in each section thereof,
   h. one of said valves being adjusted to set the peak inspiratory pressure,
   i. said other valve being adjusted to a weaker bias relative to said one valve to set the end expiratory pressure,
   j. each of said valves permitting a controlled flow of breathing gas from said outlets of said each section to the atmosphere,
   k. each of said over-pressure valves being separately adjustable so that the respective biasing forces of said two valves may be established to attain the respective desired positive peak inhalation and positive end exhalation pressures in the patient circuit,
   l. said valve said other valve therein comprising an outlet port structured for and subject to being finger occluded, whereby the operator manually, and with a single finger, establishes the duration and frequency of the inhalation and exhalation breathing cycle.

2. A device as in claim 1, wherein said tubes are highly flexible.

3. A device as in claim 1, wherein said valve housing sections are perpendicular to each other.

4. A device as in claim 1, wherein said first valve housing section is in line with said expiratory tube.

5. A device as in claim 1, wherein said second valve housing section is normal to said expiratory tube.

6. A device as in claim 1, wherein
   a. said inspiratory tube being of light weight, flexible material,
   b. said expiratory tube being of light weight, flexible material,
   c. said patient adaptor, said valve housing and said patient connector being extremely light in weight, whereby
   d. a small compact light weight package, said entire device being folded into said package which may be placed in a small handbag for ease of transport.

7. A device as in claim 6, wherein said light weight package is a compact roll of the size to substantially fit in an adult's outstretched hand.

8. A device for manual ventillation of a patient in a patient circuit, comprising:
   a. breathing gas source,
   b. a main inspiratory tube having a bore completely therethrough,
   c. one end of said inspiratory tube being attached to said breathing gas source,
   d. adapter means having an inlet port and two outlet ports,
   e. the other end of said inspiratory tube attached to said inlet port,
   f. a main expiratory tube having a bore completely therethrough,
   g. one end of said expiratory tube being attached to one outlet port of said adaptor means,
   h. a patient connector means attached to the other outlet port of said adaptor means,
   i. a two arm valve housing defining first and second normally oriented flowpaths and having an adjustable, normally closed over-pressure valve in each flowpath, said first arm being attached to and in alignment with the other end of said expiratory tube,
   j. said over-pressure valve in said first arm being of a weaker bias than the other overpressure valve,
   k. a first outlet in said second arm of said valve housing communicating said second flowpath to atmosphere,
   l. a second outlet in said first arm communicating said first flow path to atmosphere,
   m. said first outlet comprising an outlet port having a size configuration intended for and susceptible of being occluded by a typical size human finger,
   n. said finger action resulting in increasing and reducing pressure of the breathing gas in the patient circuit, o. each of said over-pressure valves being separately adjustable so that the respective biasing forces of said two valves may be established to attain the respective desired positive peak inhalation and positive end exhalation pressures in the patient circuit, and wherein said adjustable valve in said first arm always maintains a weaker bias than the other valve.

9. A device as in claim 8, wherein said adaptor means and said patient connector means are located within a confined patient area, and wherein said two arm valve housing is located remote from said confined patient area.

10. A device as in claim 8, wherein said outlet port comprises a pliable material end member.

11. A device as in claim 1 or 8, wherein a manometer is attached through a long flexible tube to said adaptor means.

* * * * *